United States Patent
Leiden

(12) 
(10) Patent No.: US 6,194,632 B1
(45) Date of Patent: Feb. 27, 2001

(54) MOUSE MODEL FOR CONGESTIVE HEART FAILURE

(76) Inventor: Jeffrey M. Leiden, 51 Cresent Dr., Glencoe, IL (US) 60022

( * ) Notice: Subject to any disclaimer, the term of this patent is extended or adjusted under 35 U.S.C. 154(b) by 0 days.

(21) Appl. No.: 09/215,098

(22) Filed: Dec. 18, 1998

Related U.S. Application Data

(60) Provisional application No. 60/068,011, filed on Dec. 18, 1997.

(51) Int. Cl.[7] .................... A01K 67/00; A01K 67/027; C12N 15/00; G01N 33/00

(52) U.S. Cl. .................... 800/3; 800/8; 800/9; 800/18; 435/320.1

(58) Field of Search ................................ 800/3, 8, 9, 13, 800/18, 21; 435/320.1

(56) References Cited

PUBLICATIONS

Chopra et al. Indian Heart Journal. 43(6): 415–420. 1991.*
Mullins et al. J. Clin. Invest. Supplement. 98(11): S37–40, Dec. 1996.*
Palmiter, RD. Ann. Rev. Genet. 20: 465–99, 1986.*
FEntzke et al. Circulation. Supplement. 96(8): pp.1740, Oct. 1997.*
Masquilier et al. Cell Growth and Differentiation. 4(11): 931–7, Nov. 1993.*
Lamph et al. Proc. Natl. Acad. Sci. USA. 87(11): 4320–4, Jun. 1990.*
Muller et al. Circulation. 92(8):2041–3, Oct. 1995.*
Palermo et al. Cell. Mol. Biol. Res. 41(6): 501–9, 1995.*
Pollick, et al. "Echocardiographic and Cardiac Doppler Assessment of Mice", *Journal of the American Society of Echocardiography* (1995) vol. 8, No. 5, part 1, pp. 602–610.
J. G. Edwards, et al. "Cardiomyopathy in Transgenic myf5 Mice", *Circulation Research* (1996) vol. 78, No. 3, pp. 379–487.
Jun Xing, et al. "Coupling of the RAS–MAPK Pathway to Gene Activation by RSK2, a Growth Factor–Regulated CREB Kinase", *Science* (1996) vol. 273, pp. 959–963.
Montminy et al. "Binding of a nuclear protein to the cyclic–AMP response element of the somatostatin gene" *Nature* (1987) vol. 328, pp. 175–178.
Fentzke, et al. "Evaluation of Ventricular and Arterial Hemodynamics in Anesthetized Closed–chest Mice" *Journal of the American Society of Echocardiography* (1997) vol. 10, No. 9, pp. 915–925.
Bristow et al., "Decreased Catechloamine Sensitivity and β–Adrenergic–Receptor Density in Failing Human Hearts" *The New England Journal of Medicine*(1982) vol. 307, No. 4, pp. 205–211.
Yao et al., "Elevated DNase I Levels in Human Idiopathic Dilated Cardiomyopathy: an Indicator of Apoptosis?", *J. Mol Cell Cardiol.* (1996) vol. 28, pp. 95–101.

Sharov et al., "Evidence of Cardiocyte Apoptosis in Myocardium of Dogs with Chronic Heart Failure", *American Journal of Pathology (1996) vol. 148 No.1*, pp. 141–149.
Krajinovic et al., "Linkage of Familial Dilated Cardiomyopathy to Chromosome 9", *Am. J. Hum. Genet.* (1995) 57:846–852.
Gulick et al., "Isolation and Characterization of the Mouse Cardiac Myosin Heavy Chain Genes*", *The Journal of Biological Chemistry*(1991) vol. 266, No. 14, pp. 9180–9185.
Subramaniam et al., "Tissue–specific Regulation of the α–Myosin Heavy Chain Gene Promoter in Trangenic Mice*", *The Journal of Biological Chemistry*(1991) vol. 266, No. 36, pp. 24613–24620.
Palermo et al., "Trangenic Remodeling of the Contractile Apparatus in the Mammalian Heart", *Circulation Research – Rapid Communication*(1996) vol. 78, pp. 504–509.
Hoit et al., "In Vivo Echocardiographic Detection of Enchanced Left Ventricular Function in Gene–Targeted Mice With Phospholamban Deficiency", *Circulation Research*(1995) vol. 77, No. 3, pp. 632–637.
Taylor et al., "Assignment of the Human Gene for CREB1 to Chromosome 2q32.3–q34", *Genomics*(1990), vol. 7, pp. 416–421.
Manning et al., "Echocardiographically Detected Myocardial Infarction in the Mouse", *Laboratory Animal Science*(1993), vol. 43, No. 6 pp. 583–585.
Michels et al., "The Frequency of Familial Dilated Cardiomyopathy in a Series of Patients with Idiopathic Dilated Cardiomyopathy", *The New England Journal of Medicine*(1992), vol. 326, No. 2, pp. 77–82.
Cohn, et al., "Effect of Vasodilator Therapy on Mortality in Chronic Congestive Heart Failure", *The New England Journal of Medicine*(1986), vol. 314, No. 24, pp. 1547–1552.
The Concensus Trial Study Group, "Effects of Enalapril on Mortality in Severe Congestive Heart Failure"(1987), vol. 316, No. 23, pp. 1429–1435.
Narula et al., "Apoptosis in Myocytes in End–Stage Heart Failure"(1996), vol. 335, No. 16, pp. 1182–1189.
Arias et al., "Activation of cAMP and mitogen responsive genes relies on a common nuclear factor ", *Nature*(1994), vol. 370, pp. 226–229.
Struthers et al., "Somatotroph hypoplasis and dwarfism in trangenic mice expressing a non–phosphorylatable CREB mutant", *Nature*(1991), vol. 350, pp. 622–624.
Chrivia et al., "Phosphorylated CREB binds specifically to the nuclear protein CBP", *Nature*(1993), vol. 365, pp. 223–226.

(List continued on next page.)

Primary Examiner—John L. LeGuyader
Assistant Examiner—Carrie Stroup
(74) Attorney, Agent, or Firm—Brinks Hofer Gilson & Lione

(57) ABSTRACT

The present invention relates to transgenic mice which express CREB. These transgenic mice provide a genetic model of dilated cardiomyopathy.

13 Claims, 6 Drawing Sheets

OTHER PUBLICATIONS

Kwok et al., "Nuclear protein CBP is a coactivator for the transcription nuclear factor CREB", *Nature*(1994), vol. 370, pp. 223–226.

Yamamoto et al., "Phosphorylation–induced binding and transcriptional efficacy of nuclear factor CREB", *Nature*(1988), vol. 334, pp. 494–498.

Gonzalez et al., "A cluster of phoshorylation sites on the cyclic AMP–regulated nuclear factor CREB predicted by its sequence", *Nature*(1989), vol. 337, pp. 749–752.

Hoeffler et al., "Cyclic AMP–Responsive DNA–Binding Protein: Structure Based on a Cloned Placental cDNA", *Science*(1988), vol. 242, pp. 1430–1433.

Sheng et al., "CREB: A $Ca^{2+}$–Regulated Transcription Factor Phosphorylated by Calmodulin–Dependent Kinases", *Science*(1991), vol. 252, pp. 1427–1430.

Ginty et al., "Nerve Growth Factor Activates a Ras–Dependent Protein Kinase That Stimulates *c–fos*Transcription via Phosphorylation of CREB", *Cell*(1994), vol. 77, pp. 713–725.

Gonzalez et al., "Cyclic AMP Stimulates Somatostatin Gene Transcription by Phosphorylation of CREB at Serine 133", *Cell*(1989), vol. 59, pp. 675–680.

Arber et al., "MLP–Deficient Mice Exhibit a Disruption of Cardiac Cytoarchitectual Organization, Dilated Cardiomyopathy, and Heart Failure", *Cell*(1997), vol. 88, pp. 393–403.

Geisterfer–Lowrance et al., "A Mouse Model of Familial Hypertrophic Cardiomyopathy", *Science*(1996), vol. 272, pp. 731–734.

Milano et al., "Enchanced Myocardial Function in Trangenic Mice Overexpressing the $\beta_2$–Adremergoc Receptor", *Science*(1994), vol. 264, pp. 582–586.

Koch et al., "Cardiac Function in Mice Overexpressing the β–Adrenergic Receptor Kinase or a βARK Inhibitor", *Science*(1995), vol. 268, pp. 1350–1353.

Barton et al., "Defective thymocyte proliferation and IL–2 production in transgenic mice expressing a dominant–negative form of CREB", *Nature*(1996), vol. 379, pp. 81–85.

Kass et al., "A gene detect that causes conduction system disease and dilated cardomyopathy maps to chromosome 1p1–1q1", *Nature Genetics*(1994), vol. 7, pp. 546–551.

Packer et al., "Effect Of Oral Milrinone On Mortality In Severe Chronic Heart Failure", *The New England Journal of Medicine*(1991), vol. 325, No. 21, pp. 1468–1475.

Pfeffer et al., "Effect of Captopril on Mortality and Morbidity in Patients with Left Ventricular Dysfunction after Myocardial Infarction", *The New England Journal of Medicine*(1992), vol. 327, No. 10, pp. 669–677.

The SOLVD Investigators, "Effect of Enalapril on Survival in Patients with Reduced Left Ventricular Ejection Fractions and Congestive Heart Failure", *The New England Journal of Medicine*(1991), vol. 325, No. 5, pp. 293–302.

Codd et al., "Epidemiology of Idiopathic Dilated and Hypertrophic Cardiomyopathy", *Circulation*(1989), vol. 80, No. 3, pp. 564–572.

Dec et al., "Idiopathic Dilated Cardiomyopathy", *The New England Journal of Medicine*(1994), vol. 331, No. 23, pp. 1564–1575.

Gardin et al., "Enhocardiographic Assessment of Left Ventricular Mass and Systolic Fuction in Mice ", *Circulation Research*(1995), vol. 76, No. 5, pp. 907–914.

Joel F. Habener, "Cyclic AMP Response Element Binding Proteins: A Cornucopia of Transcription Factors", *Molecular Endocrinology*(1990), vol. 4, No. 8, pp. 1087–1094.

Lamph et al., "Negative and positive regulation by transcription factor cAMP response element–binding protein is modulated by phosphorylation", *Proc. Natl. Acad. Sci. USA*(1990), vol. 87, pp. 4320–4324.

Müller et al., "In Vivo Isoproterenol Treatment Leads To Downregulation of the mRNA Encoding the cAMP Response Element Binding Protein in the Rat Heart", *Biochemical and Biophysical Research Communications*(1995), vol. 215, No. 3, pp. 1043–1049.

Jay N. Cohn, M.D., "The Management of Chronic Heart Failure", *The New England Journal of Medicine*(1996), vol. 335, No. 7, pp. 490–498.

Mario Vallejo, "Transcriptional Control of Gene Expression", *Journal of Neuroendocrinology*(1994), vol. 6, pp. 587–596.

McMinn, Jr. et al., "Hereditary Dilated Cardiomypathy", *Clin. Cardiol.* (1995), vol. 18, pp. 7–15.

Ofir et al., "CREB represses transcription of fos promoter: role of phosphorylation", *Gene Expression*(1991), vol. 1, No. 1, pp. 55–60.

Durand et al., "Molecular and Clinical Aspects of Inherited Cardiomypathies", *Annals of Medicine*(1995), vol. 27, No. 311–317.

Massie, M.D. et al., "Congestive Heart Failure: Current Controversies and Future Prospects", *The American Journal of Cardiology*(1990), pp. 429–430.

Bristow, M.D. "β–Adrenergic Pathways in Nonfailing and Failing Human Ventricular Myocardium", *Circulation*(1990), Supp. 1, vol. 82, pp. 1–12–125.

Carl V. Leier, M.D., "Current Status of Non–Digitalis Positive Inotropic Drugs", *The American Journal of Cardiology*(1992), vol. 69, pp. 120G–129G.

Müller et al., "cAMP Response Element Binding Protein Is Expressed and Phosphorylated in the Human Heart", *Circulation*(1995), vol. 92, No. 8, pp. 2041–2043.

* cited by examiner

- pSPT BM 21 plasmid backbone (EcoRI changed to XhoI, SmaI to BsmI)
- -4691 to +1071 (BamHI to MaeI) of alpha myosin heavy chain promoter inserted at BamHI to MluI (all sites lost) of vector
- 2668 to 2533? of SV40 complete genome (Poly A site) inserted at EcoRV of vector
- HindIII site inserted at XhoI site of vector
- $CREB_{A133}$ cDNA with 5' HA tag inserted at NotI/SalI site of vector

SEQUENCE LISTING

<160> NUMBER OF SEQ ID NOS: 5

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide containing the CREB site from the somatostatin
      promoter

<400> SEQUENCE: 1
gatcgcctcc ttggctgacg tcagagagct ag                                32

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide with a mutation in the CREB site

<400> SEQUENCE: 2
gatcgcctcc ttggctcagc acagagagct ag                                32

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide containing the AP-1 site from the metallothionein

<400> SEQUENCE: 3
tcgacgtgac tcagcgcgca gct                                          23

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence:
      HA peptide tag

<400> SEQUENCE: 4

Met Gly Tyr Pro Tyr Asp Val Pro Asp Tyr Ala
 1               5                  10

<210> SEQ ID NO 5
<211> LENGTH: 327
<212> TYPE: PRT
<213> ORGANISM: Homo sapiens

<400> SEQUENCE: 5

Met Thr Met Glu Ser Gly Ala Glu Asn Gln Gln Ser Gly Asp Ala Ala
 1               5                  10                  15

Val Thr Glu Ala Glu Asn Gln Gln Met Thr Val Gln Ala Gln Pro Gln
                20                  25                  30

Ile Ala Thr Leu Ala Gln Val Ser Met Pro Ala Ala His Ala Thr Ser
        35                  40                  45

Ser Ala Pro Thr Val Thr Leu Val Gln Leu Pro Asn Gly Gln Thr Val
    50                  55                  60

Gln Val His Gly Val Ile Gln Ala Ala Gln Pro Ser Val Ile Gln Ser

-continued

```
                65                  70                  75                  80
Pro Gln Val Gln Thr Val Gln Ile Ser Thr Ile Ala Glu Ser Glu Asp
                    85                  90                  95
Ser Gln Glu Ser Val Asp Ser Val Thr Asp Ser Gln Lys Arg Arg Glu
                100                 105                 110
Ile Leu Ser Arg Arg Pro Ser Tyr Arg Lys Ile Leu Asn Asp Leu Ser
            115                 120                 125
Ser Asp Ala Pro Gly Val Pro Arg Ile Glu Glu Lys Ser Glu Glu
            130                 135                 140
Glu Thr Ser Ala Pro Ala Ile Thr Thr Val Thr Val Pro Thr Pro Ile
145                 150                 155                 160
Tyr Gln Thr Ser Ser Gly Gln Tyr Ile Ala Ile Thr Gln Gly Gly Ala
                165                 170                 175
Ile Gln Leu Ala Asn Asn Gly Thr Asp Gly Val Gln Gly Leu Gln Thr
            180                 185                 190
Leu Thr Met Thr Asn Ala Ala Ala Thr Gln Pro Gly Thr Thr Ile Leu
            195                 200                 205
Gln Tyr Ala Gln Thr Thr Asp Gly Gln Gln Ile Leu Val Pro Ser Asn
    210                 215                 220
Gln Val Val Gln Ala Ala Ser Gly Asp Val Gln Thr Tyr Gln Ile
225                 230                 235                 240
Arg Thr Ala Pro Thr Ser Thr Ile Ala Pro Gly Val Val Met Ala Ser
                245                 250                 255
Ser Pro Ala Leu Pro Thr Gln Pro Ala Glu Glu Ala Ala Arg Lys Arg
                260                 265                 270
Glu Val Arg Leu Met Lys Asn Arg Glu Ala Ala Arg Glu Cys Arg Arg
            275                 280                 285
Lys Lys Lys Glu Tyr Val Lys Cys Leu Glu Asn Arg Val Ala Val Leu
            290                 295                 300
Glu Asn Gln Asn Lys Thr Leu Ile Glu Glu Leu Lys Ala Leu Lys Asp
305                 310                 315                 320
Leu Tyr Cys His Lys Ser Asp
                325
```

MOUSE MODEL FOR CONGESTIVE HEART FAILURE

The present application claims priority to U.S. Provisional Application Ser. No. 60/068,011, filed Dec. 18, 1997.

BACKGROUND OF THE INVENTION

The present invention relates to transgenic mice which express CREB. These transgenic mice provide a genetic model of dilated cardiomyopathy.

Congestive heart failure (CHF) is a leading cause of cardiovascular morbidity and mortality affecting more than 4 million Americans and representing the most common reason for hospitalization of patients over the age of 65 (1, 2). Idiopathic dilated cardiomyopathy (IDC), a primary myocardial disease of unknown etiology characterized by ventricular dilatation and depressed myocardial contractility is an important cause of CHF with an estimated prevalence of 36 cases/100,000 (3–7). Relatively little is known about the molecular mechanisms underlying the pathogenesis of IDC. Progress in this area has been limited by the lack of animal models that closely resemble the anatomical and clinical features of the human disease.

Several previously described genetically modified mice have been reported to develop cardiomyopathies. These include mice expressing mutant forms of α-myosin heavy chain (α-MHC), mice engineered to ectopically express the myf5 bHLH transcription factor in the heart, and mice containing targeted mutations of the muscle LIM protein (MLP) (49–51). However, the phenotypes of each of these mice differs significantly from that of the transgenic mice described herein. Unlike the transgenic mice of the present invention, which display progressive cardiac dilatation without hypertrophy, the α-MHC and myf5 mice develop a hypertrophic cardiomyopathy with myocyte disarray and interstitial fibrosis (50, 51). Consistent with these histological findings, the α-MHC mice display normal end systolic LV pressures and dP/dtmax but abnormal LV relaxation. These findings are highly reminiscent of the phenotype of patients with hypertrophic as opposed to dilated cardiomyopathy. The phenotype of the transgenic mice of the present invention also differed significantly from that of the recently described muscle LIM protein (MLP)-deficient mice which display soft, markedly hypertrophic hearts with grossly abnormal sarcomere structure within the first several weeks after birth (49). Unlike the transgenic mice of the present invention, 50–70% of the MLP-deficient mice die before 10 days of age.

SUMMARY OF THE INVENTION

Accordingly, one object of the present invention is to provide a transgenic mouse, which displays progressive cardiac dilatation without hypertrophy.

The inventor of the present application has now achieved these and other aims by overexpressing a transgene encoding CREB or by expressing a transgene encoding a dominant negative CREB molecule in mice.

DESCRIPTION OF THE EMBODIMENTS

Figure 1A:
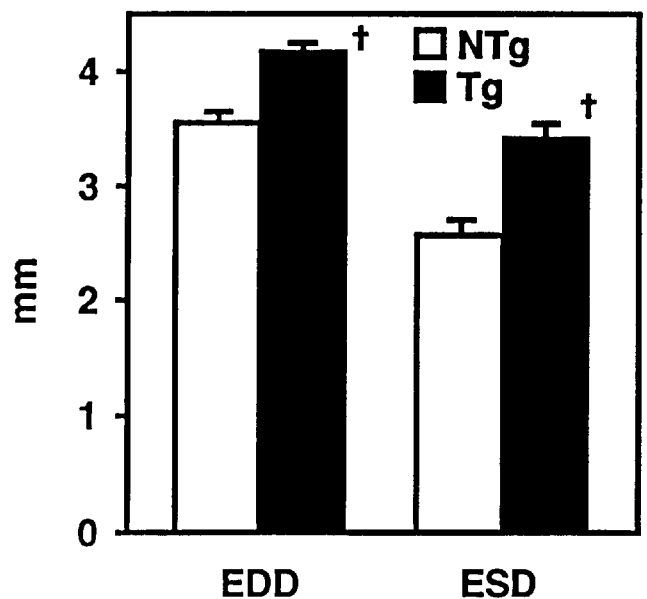
FIG. 1 M-mode echocardiographic analysis of the $CREB_{A133}$ mice. (A) End diastolic (EDD) and end systolic (ESD) left-ventriculor dimensions as determined by M-mode echocardiography in the $CREB_{A133}$ mice (Tg) (n=9) and non-transgenic control littermates (NTg) (n=10). (B) Shortening fraction at baseline (B) and following a continuous intravenous infusion of 1 ng/min isoproterenol (I) in the $CREB_{A133}$(Tg) (n=9) and non-transgenic control littermates (NTg) (n=10). Note the diminished response to isoproterenol in the $CREB_{A133}$ animals as compared to the NTg controls. The data in (A) and (B) is shown as mean±SEM. t denotes significant differences (P<0.005) between the control and Tg groups.

Idiopathic dilated cardiomyopathy (IDC) is a common primary myocardial disease of unknown etiology characterized by progressive biventricular failure, cardiac dilatation, and premature mortality. Transgenic mice overexpressing CREB or expressing a dominant-negative form of the CREB transcription factor (such as $CREB_{A133}$) under the control of the cardiac myocyte-specific promoter (such as α-MHC) develop dilated cardiomyopathy that closely resembles many of the anatomical, physiological and clinical features of human IDC.

Between 2 and 20 weeks of age, these mice develop four chamber cardiac dilatation, decreased systolic and diastolic left ventricular function, and attenuated contractile responses to the β-adrenergic agonist, isoproterenol. Histologically, the hearts of these transgenic mice demonstrated both atrophic and hypertrophied fibers as well as significant interstitial fibrosis. These anatomical and hemodynamic changes were associated with hepatic congestion and peripheral edema, intracardiac thrombi, and premature mortality. Taken together, CREB is an important regulator of cardiac myocyte function and provides a genetic model of dilated cardiomyopathy which should facilitate studies of both the pathogenesis and therapy of this clinically important disorder.

CREB is a 43 kD basic leucine zipper (bZip) transcription factor that binds to the octanucleotide sequence, TGANNTCA both as a homodimer and as a heterodimer in association with other members of the CREB/ATF and AP1 families (8–12). CREB plays a critical role in regulating gene expression in response to a variety of extracellular signals including nerve growth factor in neuronal cells (13) and antigen receptor cross-linking in T lymphocytes (14). In accordance with this invention, the cDNA of any CREB molecule (i.e., human, mouse, chicken, rat CREB and the like) can be used.

The transcriptional activity of CREB is positively regulated by phosphorylation of a critical Ser residue ($Ser_{133}$) located in the kinase-inducible domain of protein (15, 16). In the unphosphorylated state, CREB can bind to DNA but cannot activate transcription (16). Phosphorylation of CREB on $Ser_{133}$ facilitates its interaction with the 265 kD CREB binding protein (CBP) which in turn is able to interact with and activate the basal transcription complex (17–19). CREB phosphorylation and activation can be mediated by a variety of intracellular signaling pathways including (i) protein kinase A in response to elevations in intracellular cAMP (16), (ii) calmodulin kinases in response to elevations in intracellular calcium (20) and (iii) RSK2 in response to activation of a ras-dependent pathway (21). The importance of $Ser_{133}$ phosphorylation for CREB transcriptional activity is underscored by the finding that a mutant CREB molecule, $CREB_{A133}$ containing a $Ser_{133}$ to Ala substitution functions as a potent dominant negative repressor of CREB-dependent gene expression both in vitro and in vivo (22–24). The scope of this invention is not limited to replacing $Ser_{133}$ with Ala, it should be understood that $Ser_{133}$ can be substituted with any other naturally encoded amino acid residue that can not be phosphorylated.

Additionally, any other dominant negative CREB molecule can be used in this invention, including, but not limited to, a deletion mutant containing just the DNA binding and dimerization domains or a peptide just containing the kinase inducible domain. Over-expression of wild type CREB causes dilated cardiomyopathy because it also serves as a dominant negative form which overwhelms the phosphorylation machinery. Other constructs include a deletion in which the transcriptional activation domain is removed, a deletion mutant containing only the leucine zipper and basic regions, a mutant or deletion lacking DNA binding activity (i.e. mutation or deletions within the basic region DNA binding domain).

Also, overexpression of dominant negative forms of other members of the CREB/ATF family of bZip proteins which bind to the same site on DNA will also cause cardiomyopathy. Examples would include but not be limited to ATF1, ATF2, ATF4, and CREM.

Suitable cardiac myocyte-specific promoter include any promoter which directs expression of the CREB or mutant CREB molecule in myocytes, including, but not limited to, α-MHC, beta myosin heavy chain, cardiac troponin C, myosin light chain 2V, Nkx2.5 (also called Csx), cardiac tropoinin I, cardiac tropoinin T, rous sarcoma virus (RSV) LTR, and muscle creatine kinase.

Previous studies have provided evidence to suggest that CREB might be an important regulator of cardiac myocyte gene expression. The $Ser_{133}$-phosphorylated and transcriptionally active form of CREB is present in chicken (25), rat (26) and human cardiac myocytes (27). Moreover, G-protein coupled receptors such as the β-adrenergic receptors are important regulators of the contractile state of cardiac myocytes (28, 29). Such receptors mediate their effects by altering intracellular levels of cAMP, which, in turn, is an important regulator of CREB activity (16). In the rat, CREB mRNA levels have been reported to be reduced following chronic stimulation with the β-adrenergic agonist, isoproterenol (27), an experimental situation that mimics the chronic hyperadrenergic state that is thought to play a role in the progression of CHF (30–32). To test the role of CREB in regulating cardiac function in vivo, $CREB_{A133}$ transgenic mice that express a dominant-negative mutant form of CREB ($Ser_{133}$ to Ala) under the control of the cardiac myocyte-specific α-MHC promoter were produced. Between 2 and 20 weeks of age, these mice developed severe and progressive dilated cardiomyopathy that closely resembled both the anatomical and physiological features of the human disorder. They displayed cardiac dilatation, significantly reduced systolic and diastolic left ventricular function, hepatic congestion, peripheral edema, and intracardiac thrombi. Moreover, like patients with IDC, the $CREB_{A133}$ mice died prematurely. These results identify CREB as a novel transcriptional regulator of cardiac myocyte function and provide a useful genetic model for studies of the pathophysiological mechanism(s) and treatment of human dilated cardiomyopathy.

Although not required, the following theory is provides one possible mechanism which explains why the transgenic mice provide a genetic model of dilated cardiomyopathy. The inventor does not intend to be bound by this theory.

Mechanism of Dilated Cardiomyopathy in the $CREB_{A133}$ Mice

First, what is the mechanism by which the $CREB_{A133}$ protein functions as a dominant-negative transcription factor in these mice? There are at least three different molecular mechanisms by which overexpression of $CREB_{A133}$ could dysregulate CREB-dependent transcription. First, because $CREB_{A133}$ can bind to DNA but fails to activate transcription, it has been shown to displace trancriptionally active CREB from CRE sites and thereby down-regulate CREB-dependent transcription (22, 23). The EMSA data showing that the majority of the CREB binding activity in $CREB_{A133}$ nuclear extracts represents $CREB_{A133}$-containing dimers suggests that this mechanism may account for at least some of the dominant-negative effects of the transgene. Secondly, the finding of decreased phospho-CREB in the $CREB_{A133}$ cardiac nuclear extracts suggests that the $CREB_{A133}$ protein may displace wild-type CREB from the appropriate CREB kinases. $CREB_{A133}$ can dimerize with wild-type CREB as well as with other selected members of the CREB/ATF family (12). Thus, overexpression of $CREB_{A133}$ might also squelch CREB/ATF-dependent transcription by altering the balance of different CREB/ATF dimers present in the cell. This mechanism seems somewhat less likely given the fact that CREB homodimers appear to be the predominant CRE binding activity in normal cardiac myocytes and that we failed to detect novel CRE or AP-1 binding complexes in the $CREB_{A133}$ nuclear extracts. Finally, it is possible that $CREB_{A133}$ functions as a dominant-negative transcription factor by interacting with other (non-CREB/ATF) members of the transcriptional machinery. To some extent, it may be possible to determine the relative importance of these different mechanisms by producing transgenic mice that overexpress mutant forms of the CREB protein that specifically lack kinase binding, DNA binding, or dimerization activities in the heart and comparing their phenoyptes to those of the $CREB_{A133}$ animals. Regardless, of its mechanism of dominant-negative action, it should be emphasized that the dilated cardiomyopathic phenotype of the $CREB_{A133}$ mice is specific and not simply an artifact reflecting overexpression of a protein from the α-MHC heavy chain promoter because transgenic mice overexpressing comparable or greater levels of β-galactosidase, Bcl-x, or slow skeletal TnI from the same promoter do not develop cardiomyopathy.

What is the Mechanism Underlying the IDC Observed in the $CREB_{A133}$ Mice?

It is logical to postulate that CREB normally regulates the transcription of target genes that are required for the function and/or survival of cardiac myocytes and that expression of the $CREB_{A133}$ transgene product results in the dysregulated expression of these CREB target genes. Such CREB target genes might encode a wide variety of proteins including contractile proteins, proteins involved in generating energy or regulating excitation-contraction coupling and/or proteins required for cardiac myocyte growth or viability. Our studies did not reveal significant differences in contractile protein expression, or apoptosis in the $CREB_{A133}$ hearts. Therefore, we would suggest that CREB regulates the expression of other genes involved in cardiac myocyte growth, function and/or viability. The identification of these CREB target genes using differential display approaches will represent an important next step in understanding the physiological function of the CREB transcription pathway in the heart.

The CREB Pathway and Human Dilated Cardiomyopathy

The finding of DC in the $CREB_{A133}$ mice raises the possibility that CREB may be involved in the etiology of human dilated cardiomyopathy. It has been estimated that at least 20% of IDC is inherited in an autosomal dominant fashion (52). Loci for inherited IDC have recently been identified on human chromosomes 1p1–1q1 , 1q32, 3p22-p25 and 9 (6, 53–55). Because CREB maps to human chromosome 2q32.3–34 (56), it is unlikely that mutations in the CREB gene are directly responsible for the inherited dilated cardiomyopathies seen in these families. Nevertheless, our finding of inherited DC in the $CREB_{A133}$ mice directly implicates CREB as a member of a transcriptional pathway that plays a critical role in regulating cardiac myocyte function. Mutations in the genes encoding the proteins of this pathway are logical candidates for inherited DC. It will therefore be of interest to determine both the signaling pathways that regulate CREB activity in cardiac myocytes as well as the down-stream targets of CREB in these cells.

CREB may also play a secondary role in the progression of CHF in patients with dilated cardiomyopathy resulting from a wide range of primary etiologies. Previous studies have demonstrated that CREB mRNA levels are down-regulated following chronic β-adrenergic stimulation in the rat (26). Chronic β-adrenergic stimulation has also been proposed to play a major role in the progression of human heart failure (30–32). When taken together with our results, these findings suggest a model in which chronic β-adrenergic stimulation leads to CREB down-regulation, a situation that would mimic that observed in the $CREB_{A133}$ mice, and which might, therefore, lead to progressive cardiac dysfunction. If correct, this model suggests that therapies designed to increase CREB activity in the failing heart might slow the progression of CHF. It is also consistent with the previously observed adverse effects of β-adrenergic agonist therapy (57, 58) and the beneficial effects of treatment with β-blockers in patients with CHF (47, 59).

The lack of a reproducible animal model of IDC has limited our ability to understand the molecular basis of IDC, to study the early physiological changes that contribute to the progression of the disease, and to develop and test therapies for this clinically important disorder. Thus, in addition to providing us with important basic information concerning the role of the CREB transcriptional pathway in regulating cardiac myocyte function, the $CREB_{A133}$ mice will also allow us to address important pathophysiological and clinical questions about IDC. The relatively rapid clinical course of CHF in these animals will facilitate studies designed to identify new drugs that can decrease the morbidity and mortality associated with the disease. In addition, we can conveniently test the effects of other interventions such as exercise and diet both of which remain controversial in human IDC. It is now possible to obtain electrocardiograms in conscious, resting $CREB_{A133}$ mice in order to assess the role of cardiac arrhythmias in the early mortality observed in these animals and to test the feasibility of using anti-arrhythmic drugs to modify mortality rates. By breeding the $CREB_{A133}$ mice with other transgenic and knock-out mice we can test the ability of candidate genes to modify the hemodynamic and clinical abnormalities seen in these animals. Finally, it may be possible to use positional cloning to identify genes that can modify (both positively and negatively) the severity of CHF in the $CREB_{A133}$ mice.

EXAMPLES

Generation of transgenic mice. The α-MHC $CREB_{A133}$ transgene contains the human delta CREB cDNA (along with a 5' influenza hemagglutinin (HA) epitope tag) with a $Ser_{133}$ to Ala mutation as described previously (24) cloned into NotI/SalI digested pMHC, poly A vector (28, 29, 33–36). This vector contains a 5.8 kb BamHI/MaeIII fragment of the murine α-MHC gene which includes the promoter and exons 1–3 from the 5' untranslated region of the gene as well as an SV40 polyadenylation site (bp 2500 to 2700 of the SV40 genome). The transgene was linearized by digestion with HindIII and injected into the male pronucleus of fertilized single-cell CD1 embryos to produce the $CREB_{A133}$ transgenic mice. Transgenic founders were identified by Southern blot analysis of tail DNA. BamHI-digested genomic DNA was transferred to nitrocellulose membranes, and hybridized to a 442 bp radiolabeled XbaI/NotI fragment containing exons 2 and 3 from the 5' untranslated region of the murine α-MHC gene. This probe detects both the endogenous α-MHC gene and the transgene. All animal experimentation was performed in accordance with National Institutes of health guidelines, and protocols were approved by the Animal Care and Use Committee of the University of Chicago.

Northern Analysis. Total RNA was purified from mouse tissues using the TRIzol Reagent (Life Technologies, Gaithersburg, Md.). 10 μg of total RNA was subjected to Northern blot analysis as previously described (14) using a radiolabeled 520 bp KpnII/BstXI fragment (bp 143–663) of the human CREB cDNA.

Western analysis. 50 μg of nuclear extract prepared as described below (see Electrophoretic mobility shift assays)

was subjected to immunoblot analysis using the commercially available PhosphoPlus CREB kit (New England Biolabs, Beverly, Mass.) according to the manufacturer's instructions. Histologic analysis. Mouse tissues were fixed in 4% paraformaldehyde overnight at 4° C., embedded in paraffin and 4 mm sections were cut on a Jung Histocut 820 microtome. Sections were stained with hematoxylin and eosin or Masson's trichrome stain. Photomicrographs were obtained using Nikon SMZ-U or Zeiss Axiophot microscopes.

DNA laddering assay. Genomic DNA was purified from freshly isolated whole hearts, precipitated in ethanol overnight at 4° C., and collected by centrifugation at 27,000×g for 20 min to ensure recovery of small fragments of DNA. Total DNA was radiolabeled with 32P-dCTP and dGTP (800 Ci/mmol) (Amersham) using the Klenow fragment of DNA polymerase I. Radiolabeled DNA was fractionated by electrophoresis in 2% agarose gels, blotted to a Zeta-Probe membranes (BioRad, Hercules, Calif.) and autoradiographed.

Echocardiographic analysis. Anesthesia was induced with 2%–5% halothane, 95–98% O2 (Ohmeda Fluotec 3, Matrx Medical, Orchard Park, N.Y.) and animals were intubated with an 18 gauge angiocatheter. Anesthesia was maintained by ventilation (model SAR 830, CWE Inc., Ardmore, Pa.) with 1% halothane, 99% O2 at 130–150 breaths per minute and a tidal volume of 0.8–1.2 ml/min. The central aorta was catheterized via the right carotid artery with a 1.8 French micromanometer catheter (Millar, Houston, Tex.). A venous catheter (PE-10 tubing) was placed in the jugular vein. The animals were transferred to a heated water bed and EG electrodes were placed underneath the paws. High fidelity central aortic pressures were obtained using a 1.8F Millar Mikro-Tip catheter pressure transducer (model SPR-612, Millar, Houston, Tex.) introduced into the right carotid artery and advanced to the level of the ascending aorta. Analog signals from the pressure transducer and ECG were digitized using an analog to digital converter (AD3100, Real Time Devices, State College, Pa.). Digital files were recorded and analyzed with commercially available software (Atlantis and Pegasus software, Lakeshore Technologies, Chicago, Ill). Simultaneous two-dimensionally targeted M-mode echocardiographic recordings of the LV were obtained at the level of the papillary muscles from a parasternal window using an Hewlett-Packard (Andover, Mass.) Sonos 5500 and a pediatric broadband 12 MHz transducer. Isoproterenol (1 ng/min) was administered into the jugular vein at a constant rate using a syringe pump. Measurements were recorded 7 minutes following the start of the infusion. One non-transgenic animal could not be catheterized for technical reasons and 4 transgenic animals died following the induction of anesthesia. These animals were not included in the analysis. Statistically significant differences between groups were determined using the unpaired Student's t test. Shortening fraction was calculated as (EDD-ESD/EDD)×100.

Cardiac catheterization. Mice were anesthetized with 100 mg/kg ketamine, 5 mg/kg xylazine, and 1 mg/kg buprenorphine, intubated with an 18 gauge angiocatheter, and ventilated at 130–150 breaths per minute with a 0.8–1.2 ml tidal volume using 100% O2 as described above. The LV was catheterized via the right carotid artery using a 1.8 French micromanometer catheter (model SPR-612, Millar, Houston, Tex.). Baseline central aortic pressures were recorded before advancing the catheter into the LV. Ten second bursts of pressure and ECG tracings were recorded and analyzed as described above. Isoproterenol 40 ng/kg (in phosphate buffered saline) was administered directly into the jugular vein. Recordings were taken 20, 30 and 40 seconds following administration of isoproterenol and 5 seconds of data representing the maximal stimulation were used to calculate isoproterenol responses. Two non-transgenic animals could not be catheterized for technical reasons and 4 transgenic mice died following the induction of anesthesia. These mice were not included in the analysis. Statistically significant differences between groups were determined using the unpaired Student's t test.

Electrophoretic Mobility Shift Assays. Nuclear extracts were prepared from 8 week old $CREB_{A133}$ and wild-type hearts. Freshly isolated hearts were washed in ice cold PBS with 10 mM EDTA. Ventricles were isolated, finely minced with a razor blade and homogenized in 5 ml of Buffer A (10 mM Hepes pH 7.9, 1.5 mM $MgCl_2$, 10 mM KCl, 0.5 mM DTT, 1.0 mM PMSF) in a 7 ml glass Dounce tissue grinder using piston B. The homogenate was centrifuged at 5640×g for 15 minutes. The pellet was resuspended in 5 ml of Buffer A, rehomogenized and recentrifuged. The second pellet was resuspended in 2 ml of Buffer B (25% glycerol, 20 mM Hepes pH 7.9, 550 mM NaCl, 1.5 mM $MgCl_2$, 0.2 mM EDTA, 0.5 mM DTT, 1.0 mM PMSF, 1 mM benzamidine, 5 mg/ml aprotinin, 1 mg/ml antipain, 1 mg/ml pepstatin A, 1 mg/ml leupeptin, 20 mM chymostatin) and homogenized using piston A. The homogenate was centrifuged at 14,000 RPM in a microfuge, and the supernatant was dialyzed for 4 hours against 20% glycerol, 15 mM Hepes pH 7.9, 40 mM KCl, 1 mM EDTA, 0.5 mM DTT, 1.0 mM PMSF. All procedures were performed on ice or at 4 C. Protein concentrations were determined using the BioRad Protein Assay (BioRad, Hercules Calif.). Extracts were stored in aliquots at −70° C. For electrophoretic mobility shift assays, 11 ug of nuclear extract was mixed with 20,000 CPM of radiolabeled oligonucleotide probe (see below) in 10 mM Tris, pH 7.5, 100 mM NaCl, 4% glycerol, 1 mM EDTA, 5 mM DTT, 100 mg/ml BSA, and 67 mg/ml poly dI:dC at room temperature for 20 minutes. Complexes were fractionated by electrophoresis in 4% T, 3.2% C polyacrylamide gels in 1×TGE (100 mM Tris, 760 mM glycine, 4 mM EDTA) (100 V for 2.5 hours at room temperature). Gels were dried and subjected to autoradiography. As a control, a binding reaction containing in vitro translated CREB protein was run in parallel on each gel. The oligonucleotide probes used in these studies were the CREB site from the somatostatin promoter (SOM) and the AP-1 site from the metallothionein promoter. As a negative control, an oligonucleotide with a mutation in the CREB site which prevents binding (mSOM) was used:

CREB (SOM) (SEQ ID NO:1): 5' GATCGCCTCCTTG-GCTGACGTCAGAGAGCTAG 3' mCREB (mSOM) (SEQ ID NO:2): 5' GATCGCCTCCTTG-GCTCAGCACAGAGAGCTAG 3'

AP-1 (MTT) (SEQ ID NO:3): 5' TCGACGTGACT-CAGCGCGCAGCT 3'

For antibody supershift experiments 2 μl of antibody were added to the binding reactions and incubated at room temperature for 20 minutes. Antibodies used for these studies were anti-CREB (24H4B, Santa Cruz Biotech, Santa Cruz, Calif.), anti-HA (3F10, 0.5 mg/ml, Boehringer Mannheim, Indianapolis, Ind.), anti-NF-kB (NF-kB p65(A)-G, Santa Cruz Biotech).

RESULTS

Production and Molecular Characterization of $CREB_{A133}$ Transgenic Mice

To test directly the role of CREB in cardiac myocyte function, transgenic mice that express a dominant-negative form of CREB ($CREB_{A133}$) under the transcriptional control of the cardiac-specific α-MHC promoter were produced. This mutant CREB protein which contains an Ala for Ser substitution at aa 133 cannot be phosphorylated (and activated) and has been shown previously to function both in vitro and in vivo as a potent dominant-negative inhibitor of CREB-dependent transcription (22–24). Tissue-specific expression of this molecule in transgenic mice has been used to elucidate the role of CREB in the development and function of both anterior pituitary cells (24) and T cells(14). The α-MHC promoter (33, 34) has been used extensively in previous transgenic models (28, 29, 35, 36). This promoter is expressed in both embryonic and adult atrial myocytes. However, its expression in ventricular myocytes is restricted to post-natal and adult life.

Two independently-derived $CREB_{A133}$ founders (Tg1 and Tg2) were produced containing approximately 20 and 50 copies, respectively, of the transgene as assessed by Southern blot analysis (Southern blot analysis was performed on tail DNA from two independently-derived $CREB_{A133}$ transgenic (Tg1 and Tg2) mice and one non-transgenic control littermate (NTg). The probe detected both the endogenous α-MHC gene (αMHC) and the transgene (αMHC $CREB_{A133}$)). Northern blot analysis demonstrated that expression of the $CREB_{A133}$ transgene was restricted to the heart (Northern blot analysis of $CREB_{A133}$ expression in organs from a transgenic $CREB_{A133}$ mouse. The probe used in these experiments hybridized to the human transgene mRNA but not to the endogenous mouse CREB mRNA. To ensure equal loading, gels were stained with ethidium bromide to visualize 28S RNA (28S) prior to transfer to nylon membranes.). Because the $CREB_{A133}$ protein contained an HA epitope tag it could be distinguished from endogenous wild-type CREB on Western blots by both its increased molecular weight and by its specific immunoreactivity with an anti-HA antiserum. The $CREB_{A133}$ hearts contained an excess of $CREB_{A133}$ as compared to wild-type endogenous CREB. Western blotting of cardiac nuclear extracts with an antiserum specific for the $Ser_{133}$-phosphorylated and transcriptionally active form of CREB demonstrated that wild-type hearts contained easily detectable levels of pCREB (Western blot analysis of CREB and phospho-CREB (pCREB) expression in cardiac nuclear extracts from non-transgenic control (NTg) and $CREB_{A133}$ transgenic mice (Tg). Note the slower electrophoretic mobility of the transgenic $CREB_{A133}$ protein due to inclusion of the HA epitope tag and the absence of detectable pCREB in the $CREB_{A133}$ cardiac nuclear extracts. Equal protein loading was verified by equivalent intensities of non-specific background bands.). In contrast, no transcriptionally active pCREB was detectable in the $CREB_{A133}$ cardiac nuclear extracts.

Electrophoretic mobility shift assays (EMSAS) using nuclear extracts from wild-type mice demonstrated that CREB homodimers are the major CRE binding activity present in normal hearts (Electrophoretic mobility shift analyses (EMSA) of CRE binding activities in $CREB_{A133}$ cardiac nuclear extracts were performed with radiolabeled probes containing intact (SOM) or mutant (mSOM) CREB sites from the somatostatin promoter and nuclear extracts from $CREB_{A133}$ (Tg) or wild-type littermate control (NTg) hearts. For supershift experiments, antibodies against CREB, HA, or NF-kB were added to the binding reactions.). This conclusion was based on the findings that the single major band in the wild-type CRE EMSA displayed an identical electrophoretic mobility to in vitro translated CREB protein and was quantitatively supershifted by a CREB-specific antibody but not by control antibodies to the hemagglutinin epitope tag (α-HA) or the NF-kB transcription factor. Nuclear extracts from the $CREB_{A133}$ hearts contained approximately 2–3 fold more CREB binding activity than extracts from the wild-type hearts. This increased CREB binding activity which displayed an identical electrophoretic mobility to CREB homodimers was due to expression of the $CREB_{A133}$ protein because approximately ⅔ of the binding activity in these extracts could be supershifted by the α-HA antibody which is specific for the HA-tagged $CREB_{A133}$ transgene protein. Because CREB has been reported to be capable of heterodimerizing with some AP1 family members (22, 23), EMSAs with a radio-labeled AP1 probe were also performed. Both wild-type and $CREB_{A133}$ cardiac nuclear extracts contained barely detectable but equivalent levels of AP1 binding activity. Taken together, these results demonstrated that (i) CREB homodimers are the predominant CREB binding activity in wild-type hearts, (ii) the $CREB_{A133}$ mice display cardiac-specific overexpression of a dominant-negative form of CREB and (iii) overexpression of $CREB_{A133}$ in the heart results in undetectable levels of transcriptionally active nuclear pCREB and (iv) the $CREB_{A133}$ protein present in cardiac extracts from $CREB_{A133}$ transgenic mice binds efficiently to CRE but not to AP1 sites.

Pathological Evidence of Dilated Cardiomyopathy in the $CREB_{A133}$ Mice

Detailed pathological, echocardiographic and hemodynamic analyses were performed on mice derived from the first $CREB_{A133}$ founder (Tg1) and confirmed in a second founder line (Tg2). The $CREB_{A133}$ mice demonstrated both gross and histological evidence of dilated cardiomyopathy. At necropsy, the hearts from adult $CREB_{A133}$ animals displayed marked four chamber dilatation and, in many animals, both the ventricles and the atria were found to contain thrombi in various states of organization (Pathological analyses were performed on freshly isolated hearts from $CREB_{A133}$ (Tg) and non-transgenic control (NTg) animals. Hearts were fixed in 4% paraformaldehyde, sectioned at the level of the papillary muscles, and stained with hematoxylin and eosin. Both the left (LV) and right (RV) ventricles are enlarged in the $CREB_{A133}$ heart. Marked heterogeneity in myocyte size, the presence of vacuolated myocytes, and the presence of interstitial fibrosis (which stains blue with Trichrome) were noted in the $CREB_{A133}$ heart.). Cross sections through the ventricles demonstrated biventricular enlargement without significant increases in wall thickness. Histological examination revealed marked heterogeneity in myocyte size in the $CREB_{A133}$ hearts as compared to control hearts, with some myocytes demonstrating hypertrophy and others appearing atrophied. In addition, many $CREB_{A133}$ cardiac myocytes appeared vacuolated. Staining with Masson's trichrome stain for collagen demonstrated significant interstitial fibrosis in the $CREB_{A133}$ ventricles compared to ventricles from non-transgenic control littermates. Of note, significant inflammatory cell infiltrates were not observed in the $CREB_{A133}$ hearts.

Figure 1B:
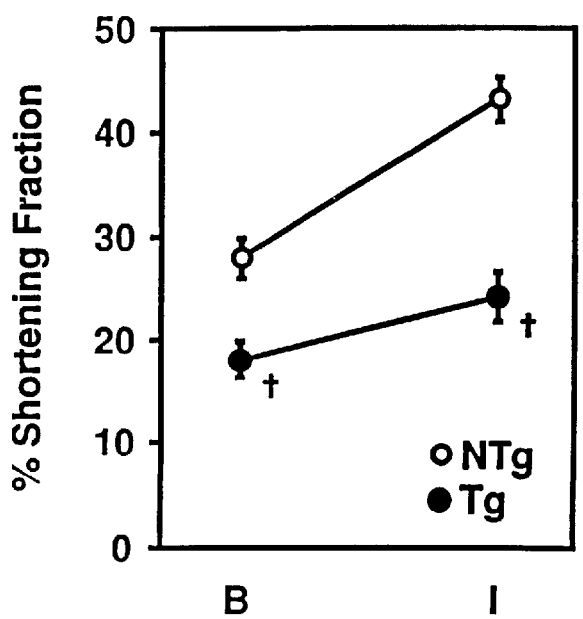

Echocardiographic Assessment of Left Ventricular Dimensions and Function in the $CREB_{A133}$ Mice Recent technological advances have made possible the echocardiographic assessment of murine cardiac structure and function (37–41). Accordingly, both the LV dimensions and systolic function of the $CREB_{A133}$ mice using two-dimensionally-targeted M-mode echocardiography acquired both at baseline and following stimulation with the β-adrenergic agonist, isoproterenol were assessed (FIG. 1). In keeping with the pathological findings of left ventricular dilatation, baseline echocardiographic analyses demonstrated 33 and 18% increases in left ventricular end systolic and end diastolic dimensions, respectively in the $CREB_{A133}$ mice as compared to the non-transgenic littermate controls (P<0.005)(FIG. 1A). Shortening fraction, the percent fractional change in LV cavity size during ventricular systole is an echocardiographic index of left ventricular systolic function. A comparison of the baseline LV shortening fractions of the $CREB_{A133}$ animals with those of non-transgenic control littermates demonstrated 35% decreases in shortening fraction in the $CREB_{A133}$ mice (P<0.005)(FIG. 1B). Increases in LV contractility in response to β-adrenergic stimulation represent one index of contractile reserve. Therefore, the LV shortening fractions of the $CREB_{A133}$ and control mice following intravenous infusion of isoproterenol were also compared (FIG. 1B). The non-transgenic control animals demonstrated a 54% increase in shortening fraction in response to treatment with isoproterenol. In contrast, the $CREB_{A133}$ mice demonstrated a significantly reduced (34%) enhancement in shortening fraction following β-adrenergic stimulation (P<0.0005). These experiments provided in vivo confirmation of the LV dilatation of the $CREB_{A133}$ mice. They also demonstrated depressed LV systolic function at baseline and decreased contractile reserve in response to β-adrenergic stimulation in these animals.

Hemodynamic Assessment of Left Ventricular Function in the $CREB_{A133}$ Mice Cardiac catheterizations using a high fidelity micromanometer catheter were performed to further analyze the left ventricular function of the $CREB_{A133}$ mice, both in the basal state and following stimulation with the β-adrenergic agonist, isoproterenol (FIG. 2). Adult $CREB_{A133}$ mice demonstrated significantly depressed LV systolic function as assessed by the maximal first derivative of the LV pressure (dP/dtmax) (FIG. 2A). At baseline, dP/dtmax was 24% less in the $CREB_{A133}$ mice as compared to non-transgenic control littermates (P<0.05). The $CREB_{A133}$ mice also displayed basal abnormalities of diastolic relaxation with 35% reductions in the maximal negative derivative of LV pressure (dP/dtmin) as compared to non-transgenic littermate controls (P<0.005). As shown in FIGS. 2C and D, non-transgenic control mice demonstrated significant enhancements of both dP/dtmax and dP/dtmin following stimulation with the β-adrenergic agonist, isoproterenol. In contrast, the $CREB_{A133}$ mice demonstrated significantly reduced responses of both dP/dtmax and dP/dtmin following isoproterenol treatment (FIGS. 2B and C)(P<0.005 for both values). Thus, the results of these experiments confirmed the echocardiographic findings and demonstrated abnormalities of both basal LV systolic and diastolic function as well as reduced responsiveness to β-adrenergic stimulation in the $CREB_{A133}$ mice.

Figure 2A:
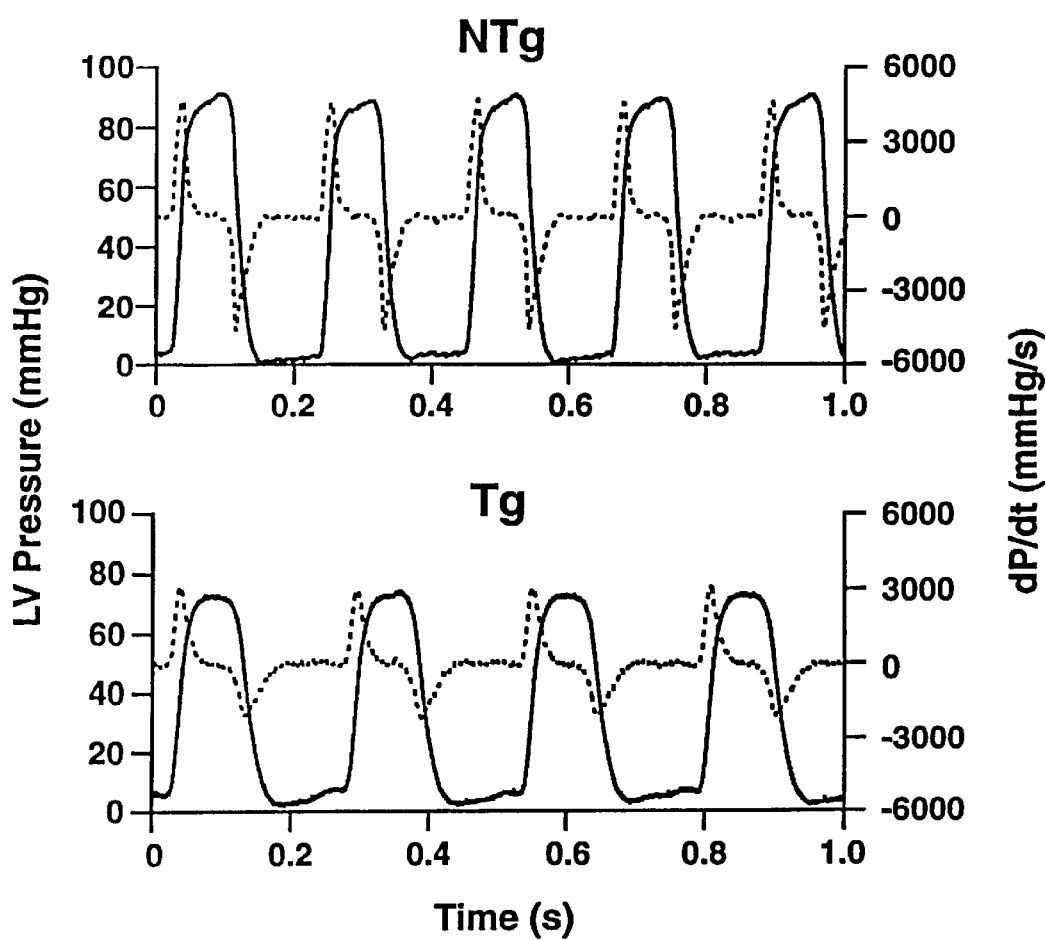
FIG. 2 Hemodynamic analyses of the $CREB_{A133}$ mice. (A) High fidelity left ventricular pressure tracings from control (NTg) and $CREB_{A133}$ transgenic (Tg) mice. The solid lines denote LV pressure, the dotted lines represent the first derivative of pressure (dP/dt). Note the reductions in both peak systolic pressure and maximum dP/dt and the decreased minimum dP/dt in the $CREB_{A133}$ animal. (B) and (C) Mean maximum and minimum dP/dt in $CREB_{A133}$(Tg) (n=10) and non-transgenic control littermates (NTg) (n=10) was measured both at baseline (B) and following treatment with a single intravenous bolus of 40 ng/kg isoproterenol (I). (D) Baseline arterial blood pressures were measured using a micromanometer catheter inserted into the central aorta via the right common carotid artery. The data is shown as mean±sem. * and t denote significant differences (P<0.05 and P<0.005, respectively) between the control and Tg groups.
Figure 2B:
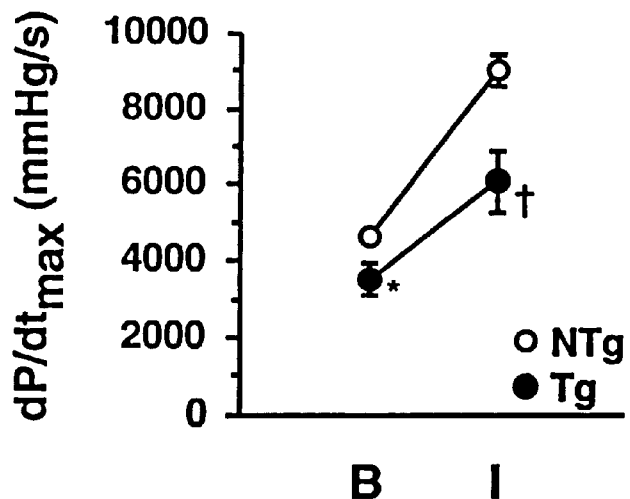
Figure 2C:
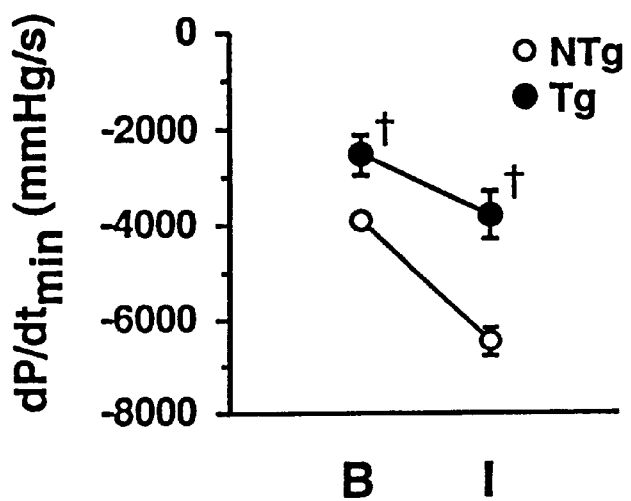
Figure 2D:
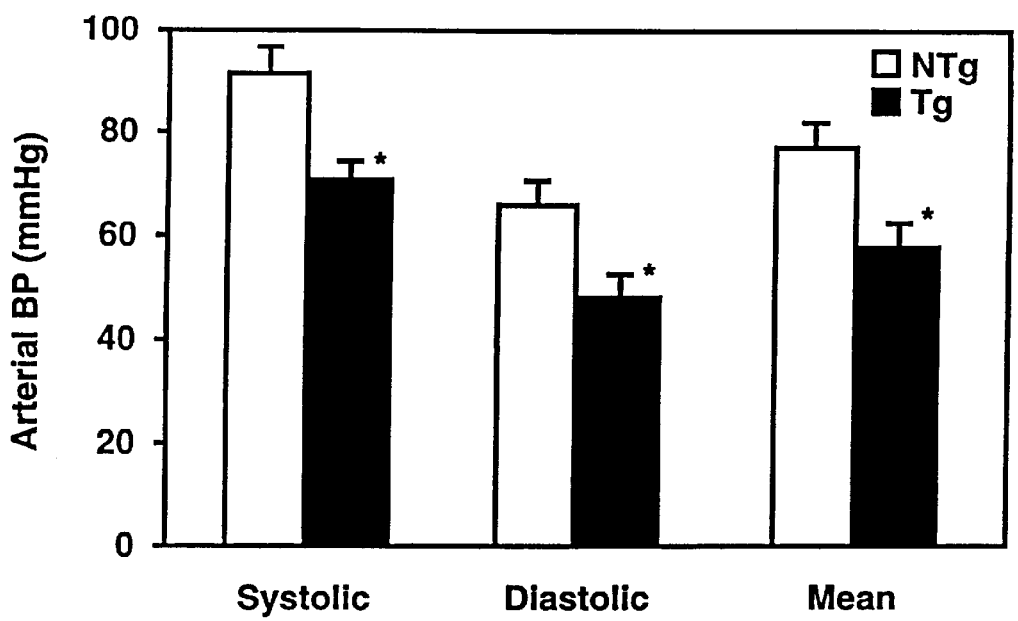

Central aortic blood pressures in the $CREB_{A133}$ mice were also monitored. The $CREB_{A133}$ mice demonstrated significant reductions in systolic, diastolic, and mean arterial blood pressures as compared to non-transgenic control littermates (P<0.05) (FIG. 2D). In humans with IDC, reductions in blood pressure are typically seen only in association with marked LV dysfunction. Therefore, the reduced blood pressure in the $CREB_{A133}$ mice likely reflected the severity of the CHF in these animals. Despite the observed reductions in blood pressure, electrocardiographic monitoring of the $CREB_{A133}$ mice did not reveal significant elevations in heart rate. This lack of tachycardia may reflect the bradycardic effects of the anesthetic agents used in these experiments and/or the relatively rapid basal heart rates of mice (400–600 beats per min).

Apoptosis and Contractile Protein Expression in the $CREB_{A133}$ Mice

Apoptosis has recently been postulated to play a role in the progression of congestive heart failure in humans (42–44). Therefore, it was of interest to determine if the dilated cardiomyopathy observed in the $CREB_{A133}$ mice was associated with increased cardiac myocyte apoptosis in these animals. Two assays were used to compare apoptosis in $CREB_{A133}$ and wild-type control hearts. A DNA laddering assay did not reveal evidence of increased apoptosis in the $CREB_{A133}$ hearts (DNA extracted from $CREB_{A133}$(Tg) or control (NTg) hearts was radiolabeled with $^{32}P$-dCTP and dGTP using the Klenow fragment of DNA polymerase I and fractionated by electrophoresis in a 2% agarose gel. In a parallel control experiment a mouse heart was subjected to 3 hours of ischemia and 5 hours of reperfusion by ligation of the left anterior descending artery and a DNA laddering assay was performed. Size markers in bp are shown to the left of the gel. Note the lack of low molecular weight DNA laddering in both the Tg and NTg hearts as compared to the heart subjected to ischemia and reperfusion. (B) SDSPAGE analysis of contractile protein expression in $CREB_{A133}$(Tg) and Control (NTg) hearts. Ventricular protein extracts were fractionated by SDS-PAGE and the resulting gel was stained with Coomassie Blue.). In control experiments, this same assay did detect increased apoptosis in a mouse model of reperfusion injury. In a second series of experiments, a TUNEL assay was used to compare the numbers of apoptotic cardiac myocytes in $CREB_{A133}$ mice and wild-type littermates. In agreement with the DNA laddering assay, there was no detectable increase in apoptotic cells in the $CREB_{A133}$ hearts. The possibility that expression of the $CREB_{A133}$ transgene caused abnormalities in contractile protein expression in the transgenic mice was also considered. However, no significant abnormalities in contractile protein expression were detected by SDS-PAGE analysis of ventricular proteins from the $CREB_{A133}$ animals. Consistent with these findings, electron microscopic analyses demonstrated normal sarcomere structure in cardiac myocytes from 8 week old $CREB_{A133}$ animals.

Clinical Course of Congestive Heart Failure in the $CREB_{A133}$ Mice

Congestive heart failure in patients with IDC is a well characterized clinical entity that results in significant morbidity and 5 year mortality rates as high as 50%(1, 45–48). Patients with end-stage CHF often suffer from both "forward failure" due to reduced cardiac output and perfusion of the vital organs and "backward failure" due to increased pulmonary and systemic venous pressures. Forward failure is often manifest by lethargy, weakness, and confusion while backward failure presents as dyspnea, peripheral edema, hepatic congestion, and ascites. Between 8 and 20 weeks of age, the $CREB_{A133}$ mice were noted to develop severe peripheral edema and ascites and to become dyspneic and lethargic, often not moving from one corner of their cages (Photographs of a 20 week old $CREB_{A133}$ mouse and a non-transgenic littermate revealed massive generalized edema in the $CREB_{A133}$ mouse.). Pathological examination revealed signs of advanced chronic hepatic congestion. Livers from the $CREB_{A133}$ animals demonstrated a classical "nutmeg" appearance with dark red areas of central venous congestion and central lobular necrosis seen by histological analyses (Gross pathology of freshly isolated livers from a $CREB_{A133}$ mouse and a non-transgenic littermate revealed a nutmeg appearance in the $CREB_{A133}$ liver. Photomicrographs of histological sections of livers were obtained from $CREB_{A133}$ and non-transgenic control littermates. Central venous congestion and the central lobular hepatocyte necrosis were noted in the $CREB_{A133}$ livers.).

Figure 3:
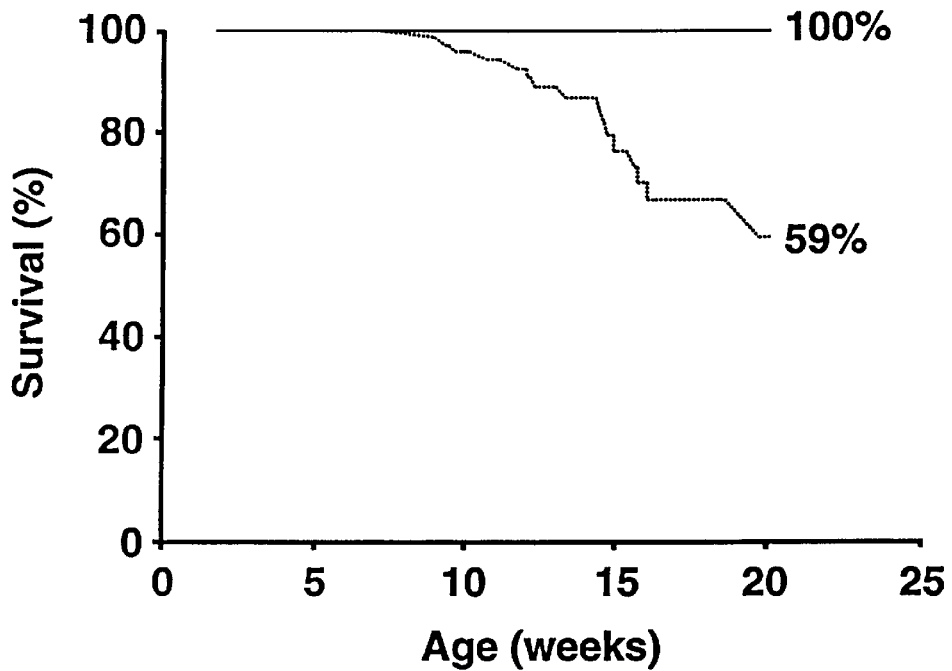
FIG. 3 Kaplan-Meier survival analysis of the $CREB_{A133}$ mice. The solid line shows the Kaplan-Meier estimate of the survivor functions of the non-transgenic control littermates. The dotted line shows the Kaplan-Meier estimate of the survivor functions of the $CREB_{A133}$ mice. The fraction of mice surviving in each group at the end of 20 weeks is noted at the right of the plot. Both groups started with 72 mice. Differences in survival rates between the Tg and NTg groups were significant by the log rank test (P<0.000005).
Figure 4:
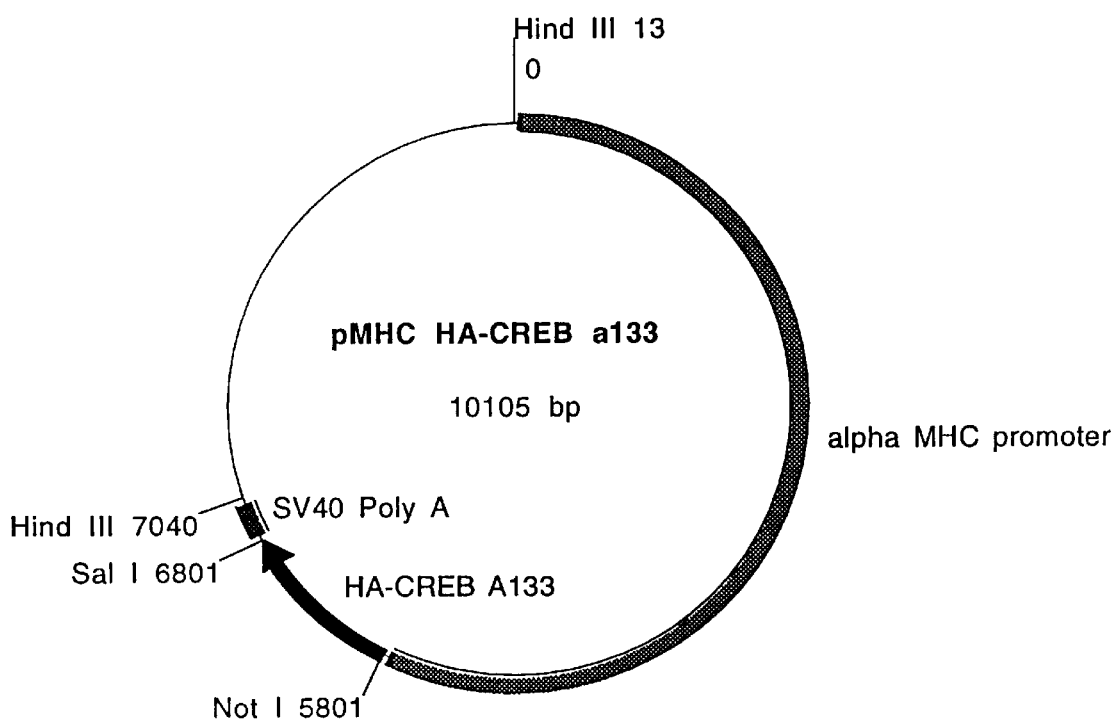
FIG. 4 is a restriction map of the plasmid used in the example section. The α-MHC $CREB_{A133}$ transgene contains the human delta CREB cDNA (along with a 5' influenza hemagglutinin (HA) epitope tag) with a $Ser_{133}$ to Ala mutation as described previously (24) cloned into NotI/SalI digested PMHC, poly A vector (28, 29, 33–36). This vector contains a 5.8 kb BamHI/MaeIII fragment of the murine α-MHC gene which includes the promoter and exons 1–3 from the 5' untranslated region of the gene as well as an SV40 polyadenylation site (bp 2500 to 2700 of the SV40 genome).
Figure 5:
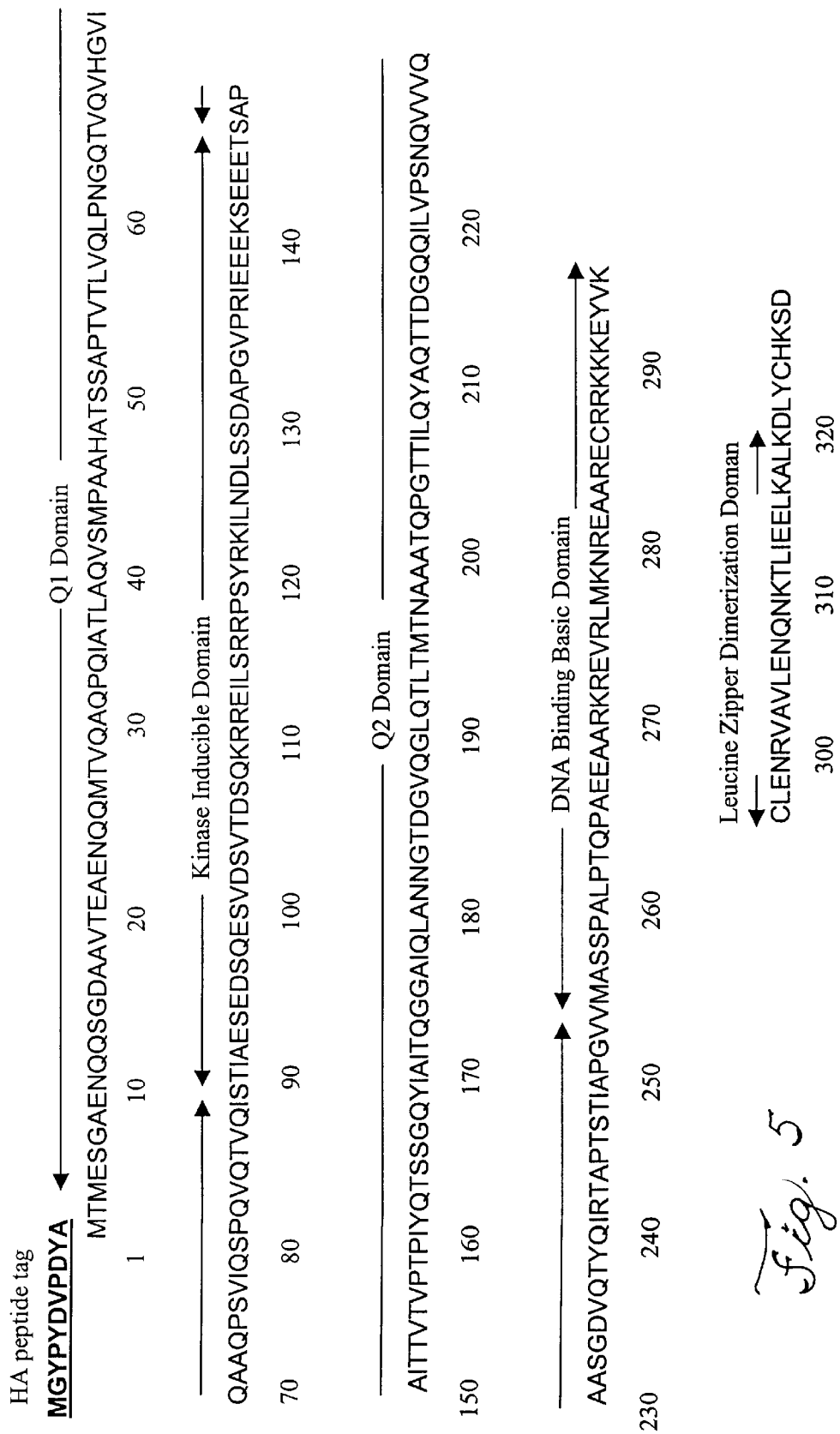
FIG. 5 is the amino acid sequence of the HA petide tag (SEQ ID NO:4) and the primary amino acid sequence of native human CREB (SEQ ID NO:5). The full DNA sequence is available in GenBank.

The $CREB_{A133}$ mice also demonstrated significantly increased mortality rates (FIG. 3). Genotypic analyses performed at 2 weeks of age revealed equivalent numbers of transgenic and non-transgenic pups suggesting that there were not significant differences in the viabilities of young $CREB_{A133}$ and non-transgenic control littermates. In contrast, between 2 and 20 weeks of age the $CREB_{A133}$ animals displayed significantly increased mortality rates as compared to the non-transgenic control mice: more than 40% of the $CREB_{A133}$ animals died by 20 weeks, whereas 100% of the non-transgenic control littermates remained alive and healthy ($P<0.000005$)(FIG. 3).

The $CREB_{A133}$ mice described herein represent a mouse model of inherited dilated cardiomyopathy that closely resembles the pathologic, hemodynamic and clinical features of the human disease. Like humans with IDC, these mice displayed progressive four chamber cardiac dilatation, interstitial cardiac fibrosis with myocyte heterogeneity and vacuolization, intra-cardiac thrombi, and signs of severe chronic venous congestion. They also demonstrated significantly depressed LV systolic function and abnormal diastolic relaxation. Finally, like patients with IDC they displayed significantly increased mortality rates. Taken together, the results identify CREB as a novel and critical transcriptional regulator of cardiac myocyte function and demonstrate that the $CREB_{A133}$ mice are a useful animal model for studies of both the pathogenesis and treatment of IDC.

REFERENCES

1. Cohn J N. The management of chronic heart failure. The New Engl. Journ. of Medicine 1996; 335:490–498.
2. Massie B M Packer M. Congestive heart failure: Current controversies and future prospects. Am. J. Cardiol. 1990; 66:429–430.
3. Davies M J ,McKenna W J. Dilated cardiomyopathy: an introduction to pathology and pathogenesis. Br. Heart Journal 1994; 72 (Supplement):S24.
4. Dec G W, Fuster V. Idiopathic dilated cardiomyopathy. The New England Journal of Medicine 1994; 331:1564–1575.
5. McMinn T R ,Ross J. Hereditary dilated cardiomyopathy. Clinical Cardiology 1995; 18:7–15.
6. Durand J-B, Abchee A B, Roberts R. Molecular and Clinical Aspects of Inherited Cardiomyopathies. Annals of Medicine 1995; 27:311–317.
7. Codd M B, Sugrue D D, Gersh B J, L. J. Melton I. Epidemiology of idiopathic dilated and hypertrophic cardiomyopathy: a population-based study in Olmsted County, Minnesota. Circulation 1989; 80:564–572.
8. Montminy M R, Bilezikjian L M. Binding of a nuclear protein to the cyclic-AMP response element of the somatostatin gene. Nature 1987; 328:175–8.
9. Gonzalez G A, Yamamoto K K, Fischer W H, Karr D, Menzel P, W. Biggs I, Vale W W, Montminy M R. A cluster of phosphorylation sites on the cyclic AMP-regulated nuclear factor CREB predicted by its sequence. Nature 1989; 337:749–752.
10. Habener J F. Cyclic AMP response element binding proteins: a cornucopia of transcription factors. [Review]. Molecular Endocrinology 1990; 4:1087–1094.
11. Hoeffler J P, Meyer T E, Yun Y, Jameson J L, Habener J F. Cyclic AMP-Responsive DNA-binding protein: structure based on a cloned placental cDNA. Science 1988; 242:1430–1433.
12. Vallejo M. Transcriptional control of gene expression by cAMP-response element binding proteins. Journal of Neuroendocrinology 1994; 6:587–596.
13. Ginty D D, Bonni A, Greenberg M E. Nerve growth factor activates a Ras-dependent protein kinase that stimulates c-fos transcription via phosphorylation of CREB. Cell 1994; 77:713–725.
14. Barton K, Muthusamy N, Chanyangam M, Fischer C, Clendenin C, Leiden J M. Defective thymocyte proliferation and IL-2 production in transgenic mice expressing a dominant-negative form of CREB. Nature 1996; 379:81–85.
15. Gonzalez G A ,Montminy M R. Cyclic AMP stimulates somatostatin gene transcription by phosphorylation of CREB at Serine 133. Cell 1989; 59:675–680.
16. Yamamoto K K, Gonzalez G A, W. H. Biggs I, Montminy M R. Phosphorylation-induced binding and transcriptional efficacy of nuclear factor CREB. Nature 1988; 334:494–498.
17. Kwok R P, Lundblad J R, Chrivia J C, Richards J P, Bachinger H P, Brennan R G, Roberts S G, Green M R, Goodman R H. Nuclear protein CBP is a coactivator for the transcription factor CREB [see comments]. Nature 1994; 370:223–6.
18. Arias J, Alberts A S, Brindle P, Claret F X, Smeal T. Karin M, Feramisco J, Montminy M. Activation of cAMP and mitogen responsive genes relies on a common nuclear factor [see comments]. Nature 1994; 370:226–9.
19. Chrivia J C, Kwok R P, Lamb N, Hagiwara M, Montminy M R, Goodman R H. Phosphorylated CREB binds specifically to the nuclear protein CBP. Nature 1993; 365:855–9.
20. Sheng M, Thompson M A, Greenberg M E. CREB: A Ca2+-regulated transcription factor phosphorylated by calmodulin-dependent kinases. Science 1991; 252:1427–1430.
21. Xing J, Ginty D D, Greenberg M E. Coupling of the RAS-MAPK pathway to gene activation by RSK2, a growth factor-regulated CREB kinase. Science 1996; 273:959–962.
22. Ofir R, Dwarki V J, Rashid D, Verma I M. CREB represses transcription of fos promoter: role of phosphorylation. Gene Expr 1991; 1:55–60.
23. Lamph W W, Dwarki V J, Ofir R, Montminy M, Verma I M. Negative and positive regulation by transcription factor cAMP response element-binding protein is modulated by phosphorylation. Proc Natl Acad Sci U S A 1990; 87:4320–4.
24. Struthers R S, Vale W W, Arias C, Sawchenko P E, Montminy M R. Somatotroph hypoplasia and dwarfism in transgenic mice expressing a non-phosphorylatable CREB mutant. Nature 1991; 350:622–4.
25. Goldspink P H Russell B. The cAMP response element binding protein is expressed and phosphorylated in cardiac myocytes. Circ. Res. 1994; 74:1042–1049.
26. Muller F U, Boknik P, Horst A, Knapp J, Linck B, Schmitz W. Vahlensieck U, Walter A. In vivo isoproterenol treatment leads to downregulation of the mRNA encoding the cAMP response element binding protein in the rat heart. Biochemical and Biophysical Research Comm. 1995; 215:1043–1049.
27. Muller F U, Boknik P, Horst A, Knapp J, Linck B, Schmitz W. Vahlensieck U, Bohm M, Deng M C, Scheld 27. [continued] HH. cAMP response element binding protein is expressed and phosphorylated in human heart. Circulation 1995; 92:2041–2043.
28. Milano C A, Allen L F, Rockman H A, Dolber P C, McMinn T R, Chien K R, Johnson T D, Bond R A, Lefkowitz R J. Enhanced myocardial function in transgenic mice overexpressing the Beta2-adrenergic receptor. Science 1994; 264:582–586.
29. Koch W J, Rockman H A, Samama P, Hamilton R, Bond R A, Milano Calif., Lefkowitz R J. Cardiac function in mice overexpressing the beta-adrenergic receptor kinase or a BetaArk inhibitor. Science 1995; 268:1350–1353.
30. Bristow M R, Ginsburg R, Minobe W, Cubicciotti R S, Sageman W S, Lurie K, Billingham M E, Harrison D C, Stinson E B. Decreased catecholamine sensitivity and beta-adrenergic-receptor density in failing human hearts. New England Journal of Medicine 1982; 307:205–211.
31. Bristow M R, Kantrowitz NE, Ginsburg R. Fowler M B. Beta-adrenergic function in heart muscle disease and heart failure. [Review]. J. Mol. Cell. Cardiol. 1985; 17 (Suppl. 2):41–52.
32. Bristow M R, Hershberger R E, Port J D, Gilbert E M, Sandoval A, Rasmussen R, Cates A E, Feldman A M. Beta-adrenergic pathways in nonfailing and failing human ventricular myocardium. Circulation 1990; 82 (suppl)I12–I25.
33. Subramaniam A, Jones W K, Gulick J, Wert S, Neumann J, Robbins J. Tissue-specific regulation of the alpha-myosin heavy chain gene promoter in transgenic mice. Journal of Biological Chemistry 1991; 266:24613–24620.
34. Gulick J, Subramaniam A, Neumann J, Robbins J. Isolation and characterization of the mouse cardiac myosin heavy chain genes. The Journal of Biological Chemistry 1991; 266:9180–9185.
35. Palermo J, Gulick J, Ng W, Grupp I L, Grupp G, Robbins J. Remodeling the mammalian heart using transgenesis. Cellular & Molecular Biology Research 1995; 41:501–509.
36. Palermo J, Gulick J, Colbert M, Fewell J, Robbins J. Transgenic remodeling of the contractile apparatus in the mammalian heart. Circulation Research 1996; 78:504–509.
37. Fentzke R C, Korcarz C E, Shroff S G, Lin H, Sandelski J, Leiden J M, Lang R M. Evaluation of ventricular and arterial hemodynamics in anesthetized, closed-chest mice. J Am Soc Echocardiography, In press 1997.
38. Manning W J, Wei J Y, Katz S E, Douglas P S, Gwathmey J K. Echocardiographically detected myocardial infarction in the mouse. Lab Anim. Sci. 1993; 43:583–585.
39. Pollick C, Hale S L, Kioner R A. Echocardiographic and cardiac Doppler assessment of mice. J. Am. Soc. Echocardiogr. 1995; 602–610.
40. Hoit B D, Khoury S F, Kranias E G, Ball N, Walsh R A. In vivo echocardiographic detection of enhanced left ventricular function in gene-targeted mice with phospholamban deficiency. Circ. Research 1995; 77:632–637.
41. Gardin J M, Siri F M, Kitsis R N, Edwards J G, Leinwand L A. Echocardiographic assessment of left ventricular mass and systolic function in mice. Circ. Research 1995; 76:907–914.
42. Narula J, Haider N, Virmani R, DiSalvo T G, Kolodgie F, Hajjar R J, Schmidt U, Semigran M J, Dec G W, Khaw B. Apoptosis in myocytes in end-stage heart failure. The New England Nournal of Medicine 1996:1182–1189.
43. Yao M, Keogh A, Spratt P, Remedios C Gd, Kiebling P C. Elevated DNase 1 levels in human idiopathic dilated cardiomyopathy: an indicator of apoptosis? J. Mol. Cell Cardiol. 1996; 28:95–101.
44. Sharov V G, Sabbah H N, Shimoyama H, Goussev A V, Lesch M, Goldstein S. Evidence of cardiocyte apoptosis in myocardium of dogs with chronic heart failure. American Journal of Pathology 1996; 148:141–149.
45. Group CT. Effects of enalapril on mortality in severe congestive heart failure: Results of the Cooperative North Scandinavian Enalapril Survival Study. N. Eng. J. Med. 1987; 316:1429–1435.
46. Cohn J N, Archibald D Z, Ziesche S. Franciosa J A, Harston W E, Tristani F E, Dunkman W B, Jacobs W, Francis G S, Flohr K H. Effect of vasodilator therapy on mortality in chronic congestive heart failure: Results of a Veterans Administration Cooperative Study (V-HeFT). New England Journal of Medicine 1986; 314:1547–1552.
47. Investigators S. Effect of enalapril on survival in patients with reduced left ventricular ejection fractions and congestive heart failure. N. Engl. J. Med. 1991; 325:293–302.
48. Pfeffer M A, Braunwald E, Moye L A, Basta L, E. J. Brown J, Cuddy T E, Davis B R, Geltman E M, Goldman S, Flaker G C. Effect of captopril on mortality and morbidity in patients with left ventricular dysfunction after myocardial infarction. Results of the survival and ventricular enlargement trial. N. Engl. J. Med. 1992; 327:669–677.
49. Arber S, Hunter J J, Ross J, Jr., Hongo M, Sansig G, Borg J, Perriard J C, Chien K R, Caroni P. MLP-deficient mice exhibit a disruption of cardiac cytoarchitectural organization, dilated cardiomyopathy, and heart failure. Cell 1997; 88:393–403.
50. Edwards J G, Lyons G E, Micales B K, Malhotra A, Factor S, Leinwand L A. Cardiomyopathy in transgenic myf5 mice. Circ Res 1996; 78:379–87.
51. Geisterfer-Lowrance A A, Christe M, Conner D A, Ingwall J S, Schoen F J, Seidman C E, Seidman J G. A mouse model of familial hypertrophic cardiomyopathy. Science 1996; 272:731–4.
52. Michels W V, Moll P P, Miller F A, Tajik J, Chu J, Driscoll D J, Burnett J C, Rodeheffer F J, Chesebro J H, Tazelaar H D. The frequency of familial dilated cardiomyopathy in a series of patients with idiopathic dilated cardiomyopathy. The New Eng. Jour. of Medicine 1992; 326:77–81.
53. Kass S, MacRae C, Graber H L, Sparks E A, McNamara D, Boudoulas H, Basson C T, P. B. Baker I, Cody R J, Fishman M C. A gene defect that causes conduction system disease and dilated cardiomyopathy maps to chromosome 1p1–q1. Nature Genetics 1994; 7:546–551.
54. Krajinovic M, Pinamonti B, Sinagra G, Vatta M, Severini G M, Milasin J, Falaschi A, Camerini F, Giacca M, Mestroni L. Linkage of familial dilated cardiomyopathy to chromosome 9. Heart Muscle Disease Study Group. Amer. J. of Hum. Genet. 1995; 57:846–852.
55. Olson T M ,Keating M T. Mapping a cardiomyopathy locus to chromosome 3p22–p25. J. of Clinic. Invest. 1996; 97:528–532.
56. Taylor A K, Klisak I, Mohandas T, Sparkes R S, Li C, Gaynor R, Lusis A J. Assignment of the human gene for CREB1 to chromosome 2q32.3q3–q34. Genomics 1990; 7:416–421.
57. Lerer C V. Current status of non-digitalis positive inotropic drugs. Am. J. Cardiol. 1992; 69:120G–128G.
58. Packer M, Carver J R, Roceheffer R J, Group PSR. Effect of oral milrinone on mortality in severe chronic heart failure. N. Engl. J. Med. 1991; 325:1468–1475.
59. Waagstein F, Bristow M R, Swedberg K. Beneficial effects of metroprolol in idiopathic dilated cardiomyopathy: a double-blind, randomized, placebo-controlled trial. Circulation 1993; 342:1441–1446.

Obviously, numerous modifications and variations of the present invention are possible in light of the above teachings. It is therefore to be understood that within the scope of the appended claims, the invention may be practiced otherwise than as specifically described herein.

What is claimed is:

1. A transgenic mouse comprising a transgene under operational control of a myocyte-specific promoter, said transgene encoding a protein having wild-type CREB activity, wherein expression of the transgene leads to congestive heart failure.

2. The trangenic mouse of claim 1, wherein the transgene comprises a native human CREB gene.

3. The transgenic mouse of claim 1, wherein the promoter is selected from the group consisting of α-MHC promoter, beta myosin heavy chain promoter, cardiac troponin C promoter, myosin light chain 2V promoter, Nkx2.5 promoter, cardiac tropoinin I promoter, cardiac tropoinin T promoter, rous sarcoma virus LTR promoter, and muscle creatine kinase promoter.

4. The transgenic mouse of claim 3, wherein the promoter is the α-MHC promoter.

5. A transgenic mouse comprising a transgene under operational control of a myocyte-specific promoter, said transgene encoding a protein having dominant negative CREB activity, wherein expression of the transgene leads to congestive heart failure.

6. The transgenic mouse of claim 5, wherein the promoter is selected from the group consisting of α-MHC promoter, beta myosin heavy chain promoter, cardiac troponin C promoter, myosin light chain 2V promoter, Nkx2.5 promoter, cardiac tropoinin I promoter, cardiac tropoinin T promoter, rous sarcoma virus LTR promoter, and muscle creatine kinase promoter.

7. The transgenic mouse of claim 6, wherein the promoter is the α-MHC promoter.

8. The transgenic mouse of claim 5, wherein the protein having dominant negative CREB activity maintains an ability to bind CRE.

9. The transgenic mouse of claim 8, wherein the protein is mutated to alter an ability of a kinase to phosphorylate the protein.

10. The transgenic mouse of claim 9, wherein the alteration comprises a change of a serine residue of native CREB to a different amino acid.

11. The transgenic mouse of claim 10, wherein the serine residue is $Ser_{133}$.

12. A method of a identifying a drug that decreases morbidity or mortality associated with congestive heart failure, comprising:

(a) administering the drug to a transgenic mouse, wherein the transgene encodes wild-type CREB or a dominant negative CREB; and (b) observing the mouse for one or more phenotypes associated with congestive heart failure.

13. The method of claim 12, wherein the phenotype is selected from the group consisting of progressive biventricular failure, cardiac dilation, decreased myocardial contractility, hepatic congestion, peripheral edema, intracardiac thrombi, and premature mortality.

* * * * *

UNITED STATES PATENT AND TRADEMARK OFFICE
CERTIFICATE OF CORRECTION

PATENT NO.    : 6,194,632 B1
DATED         : February 27, 2001
INVENTOR(S)   : Jeffrey M. Leiden Page 1 of 1

It is certified that error appears in the above-identified patent and that said Letters Patent is hereby corrected as shown below:

Title page,
OTHER PUBLICATIONS,
Line 5, delete "FEntzke" and substitute -- Fentzke -- in its place.
Line 18, delete "379-487" and substitute -- 379-387 -- in its place.
Line 49, delete "223-226" and substitute -- 855-859 -- in its place.

Claim 12,
Line 1, delete "a" before "identifying".

Signed and Sealed this

Sixteenth Day of April, 2002

Attest:

JAMES E. ROGAN
Attesting Officer
Director of the United States Patent and Trademark Office